(12) United States Patent
Rigert et al.

(10) Patent No.: US 10,744,243 B2
(45) Date of Patent: Aug. 18, 2020

(54) BREAST PUMP AND CAP FOR SAME

(71) Applicant: MEDELA HOLDING AG, Baar (CH)

(72) Inventors: Mario Rigert, Buchrain (CH); René Fischer, Zurich (CH)

(73) Assignee: MEDELA HOLDING AG, Baar (CH)

( * ) Notice: Subject to any disclaimer, the term of this patent is extended or adjusted under 35 U.S.C. 154(b) by 145 days.

(21) Appl. No.: 15/551,010

(22) PCT Filed: Feb. 9, 2016

(86) PCT No.: PCT/EP2016/052723
§ 371 (c)(1),
(2) Date: Aug. 14, 2017

(87) PCT Pub. No.: WO2016/131680
PCT Pub. Date: Aug. 25, 2016

(65) Prior Publication Data
US 2018/0028732 A1    Feb. 1, 2018

(30) Foreign Application Priority Data

Feb. 20, 2015   (EP) ...................................... 15155895

(51) Int. Cl.
*A61M 1/06* (2006.01)
*A61M 1/00* (2006.01)

(52) U.S. Cl.
CPC ............. *A61M 1/06* (2013.01); *A61M 1/0066* (2013.01)

(58) Field of Classification Search
CPC .............................. A61M 1/06; A61M 1/0066
See application file for complete search history.

(56) References Cited

U.S. PATENT DOCUMENTS 5,542,921 A   8/1996   Meyers et al.
5,776,098 A   7/1998   Silver et al.
(Continued)

FOREIGN PATENT DOCUMENTS

WO   WO-01/47577 A2    7/2001
WO   WO-2008/057218 A2   5/2008

OTHER PUBLICATIONS

International Search Report for Application No. PCT/EP2016/052723, filed Jun. 6, 2016.

*Primary Examiner* — Theodore J Stigell
(74) *Attorney, Agent, or Firm* — Marshall, Gerstein & Borun LLP

(57) ABSTRACT

A breast pump for pumping human breast milk has a flexible pumping membrane and a stiff cap, which can be fitted onto said pumping membrane, this resulting in the formation of a pumping chamber for generating a negative pressure. The cap can be, or is, connected to a breast-shield unit via a suction line. The pumping membrane has an encircling collar with a step and a laterally projecting protrusion. The cap has, on its inner side, an encircling abutment region and also at least one form-fitting element, which is spaced apart from the encircling abutment region and establishes a form fit with the protrusion of the pumping membrane. The cap is positioned with a snap fit on the pumping membrane. In the abutment region (53), it establishes a joint frictional fit with a step of the pumping membrane and thus forms a seal. The snap-fit positioning of the cap on the pumping membrane is sufficient for the cap to be retained with sealing action on the pumping membrane.

15 Claims, 6 Drawing Sheets

(56) References Cited

U.S. PATENT DOCUMENTS

| | | |
|---|---|---|
| 2004/0087898 A1 | 5/2004 | Weniger |
| 2007/0060873 A1 | 3/2007 | Hiraoka et al. |
| 2007/0135761 A1 | 6/2007 | Cheng et al. |
| 2010/0324478 A1 | 12/2010 | Kazazoglu et al. |
| 2013/0294942 A1 | 11/2013 | Stutz et al. |
| 2014/0094748 A1* | 4/2014 | Hong ............... A61M 1/06 604/74 |

* cited by examiner

BREAST PUMP AND CAP FOR SAME

CROSS-REFERENCE TO RELATED APPLICATION

The present application is the US national phase of International Application No. PCT/EP2016/052723, filed Feb. 9, 2016, which claims priority to European Application No. 15155895.4, filed Feb. 20, 2015. The priority application, EP 15155895.4, is hereby incorporated by reference.

TECHNICAL FIELD

The present invention relates to a breast pump for expressing human breast milk, and to a cap for same.

PRIOR ART

Breast pumps for expressing human breast milk have long been known. They have a vacuum pump that is operated manually or by electric motor in order to generate a negative pressure, a breast shield connected to the vacuum pump for resting on the breast, and a milk collection container connected to the breast shield for collecting the pumped milk.

U.S. Pat. No. 5,776,098 describes a breast pump having a pump diaphragm, which is connected via a drivetrain to an electric motor. The pump diaphragm is fastened in a rigid plate on a side of a soft pocket and is covered by a rigid cap. The cap bears via an inner flange in a sealing manner against a circumferential edge of the pump diaphragm. The cap is snapped onto the rigid plate via an outer flange.

WO 2001/47577 discloses a breast pump for simultaneously pumping both breasts. For this purpose it has two flexible pump diaphragms, which are arranged in an indentation in the upper side of the housing. This indentation can be closed by a cover. The pump diaphragms are each connected to a driveshaft of a motor-driven mechanism and are moved downwards and upwards in accordance with a predefined movement curve. A rigid cap can be put over each of these pump diaphragms and is connected via a suction line to the breast shield. A pump chamber is formed between the cap and moving pump diaphragm, in which pump chamber a negative pressure is generated. A suction curve is thus produced in accordance with the movement curve and applies a cyclically changing negative pressure to the breast. In one embodiment the caps are fixedly connected to the cover and are pressed onto the associated pump diaphragm when the cover is closed. In another embodiment a protective diaphragm is arranged between cap and pump diaphragm and enables a tight connection and additionally prevents a contamination of the pump diaphragm with pumped milk or bacteria. The protective diaphragm on the inner side thereof has a circumferential shoulder and a circumferential bead, which form a channel. The channel is received on a protruding edge of the pump diaphragm, whereby at the same time an airtight fit and a fastening of the cap on the pump diaphragm are provided. A check valve is arranged in the pump diaphragm in order to allow any air between pump diaphragm and protective diaphragm to escape during the first stroke. This pump is known on the market under the name "Symphony" and has proven to be very effective. It is suitable in particular for use in hospitals and in rental, since it can be used by a number of mothers on account of its protective diaphragm. Seals between two soft parts, however, are not so simple, and therefore the production of the cap, the protective diaphragm and the pump diaphragm is subject to strict specifications and requires sound knowledge accordingly.

In the meantime various breast shield units have become known in the prior art which have a media separation diaphragm in the region of the breast shield and which thus protect the pump in this way against pollutions. A breast shield unit of this type is presented for example in US 2004/0087898 and WO 2008/057218.

DISCLOSURE OF THE INVENTION

One object of the invention is therefore to create a breast pump having an alternative airtight connection between rigid cap and flexible pump diaphragm.

The breast pump according to the invention for expressing human breast milk has a motor-driven flexible pump diaphragm and a rigid cap that can be put thereover. A pump chamber for generating a negative pressure is formed between pump diaphragm and cap. The cap can be connected via a suction line to a breast shield unit or is already fixedly connected thereto, whereby the negative pressure generated in the pump chamber can be transferred into the breast shield unit. The pump diaphragm has a circumferential collar with a step. The collar also has a laterally projecting protrusion, and the cap has, on the inner side thereof, a circumferential bearing region. The cap has, on the inner side thereof, at least one form-fit element, which is arranged at a distance from the circumferential bearing region and which together with the protrusion of the pump diaphragm forms a form fit, such that the cap rests on the pump diaphragm in a manner snapped into place. The bearing region of the cap and the pump diaphragm in the region of the step are involved in a joint frictional connection and form a seal, such that the resting of the cap on the pump diaphragm in a manner snapped into place is sufficient to hold the cap in a sealing manner on the pump diaphragm and the pump and to build the pumping chamber.

The breast pump is thus assembled in a functioning manner by simply resting and snapping into place the rigid cap on the flexible pump diaphragm. The cap can thus be fitted just as easily or even more easily than the caps with protective diaphragm used until now with the Symphony pump. No additional fastening means are needed in order to connect the cap with the housing. Especially, the cap does not have to be fixed to the housing of the pump with fixing means such as screws or retaining hooks. The cap is only connected with the pump diaphragm.

In the breast pump according to the invention a protective diaphragm no longer has to be provided mandatorily between cap and pump diaphragm. In the case of the breast pump according to the invention there is preferably even no protective diaphragm and also no other part between cap and pump diaphragm, such that the cap and pump diaphragm contact one another immediately and directly at least in the region of the form fit and the frictional connection.

A defined joining force is preferably necessary in order to allow the cap to snap into place on the pump diaphragm. This joining force is preferably 5 to 50 N.

A stop is preferably provided, up to which the cap can be put over the pump diaphragm. This makes it easier for the mother to identify whether the cap is fitted correctly and completely.

The cap preferably does not snap into place on the pump diaphragm silently, but with a snap-in noise, which again or alternatively to the stop provides feedback to the mother. The mother thus receives confirmation that the breast pump is ready for use.

In a preferred embodiment a circumferential channel is formed between the bearing region and the at least one form-fit element of the cap and surrounds the collar of the pump diaphragm and receives the protrusion.

The at least one form-fit element is preferably a snap-fit element, which engages below the protrusion of the pump diaphragm.

This cap can thus be fitted in a sealing and functional manner also to the pump diaphragm of the known Symphony pump without having to use an additional protective diaphragm.

In order to avoid a lifting of the breast shield in the event of a high overpressure, in particular during the first stroke, a venting valve is arranged in the breast pump and connects the pump chamber to an outside.

In preferred embodiments the venting valve is arranged in the cap. Additionally or alternatively the venting valve is arranged in a plug connecting the suction line to the cap or in the breast shield unit or in the suction line.

The cap according to the invention for use in a breast pump can be connected via a suction line to a breast shield unit or is connected thereto. Said cap has, on the inner side thereof, a circumferential bearing region and, on the inner side thereof, at least one form-fit element, which is arranged at a distance from the circumferential bearing region in order to form a form fit with a protrusion of a pump diaphragm of the breast pump. The cap is designed in the region of the bearing region to form a frictional connection with the pump diaphragm, such that a resting of the cap on the pump diaphragm is sufficient to hold the cap in a sealing manner on the pump diaphragm.

The cap can be used in the known Symphony pump or in another breast pump with suitably designed pump diaphragm. In particular it may rest on the pump diaphragm from above in the vertical direction of the breast pump in the use position of the breast pump. If the pump diaphragm is arranged in a vertically extending side face, the cap can also be fitted in this position laterally onto the pump diaphragm. Other positions in space with respect to the pump diaphragm are also possible depending on the embodiment of the breast pump.

The cap preferably has a dome-like main body. This means that it is hemispherical and has a flattened upper face. The cap has a circumferential outermost edge, wherein the at least one form-fit element is arranged on an inner side of this outermost edge. The form-fit element is thus formed on the inner lower edge of the cap. This form is particularly suitable for being fitted on a pump diaphragm which is likewise dome-like, in particular on the pump diaphragm of the known Symphony pump.

The dome-like main body preferably transitions into an edge region that is chamfered in a manner widening outwardly and which transitions into a cylindrical edge region, the cylindrical edge region ending in the outermost edge. The circumferential bearing region is preferably formed in the region of transition from the main body into the chamfered edge region. This design also enables an optimal use with a pump diaphragm itself having a cylindrical collar or surface, as is the case for example with the pump diaphragm of the Symphony pump.

The outermost edge is preferably circular.

The at least one form-fit element is preferably designed as a snap-fit element. The at least one form-fit element is preferably an inwardly directed bead. The at least one form-fit element is preferably formed in a manner running around the inner side of the cap. A number of form-fit elements are preferably provided and are separated from one another by interruptions. Three form-fit elements and three interruptions are preferably provided. The three form-fit elements are preferably identical. This segment-like form fit can allow air to escape to a small extent from the chamber in the event of increased overpressure.

In a preferred embodiment three snap-fit segments are thus provided, which extend over the inner periphery of the cap in a uniformly distributed manner and at the same height. The form-fit elements are used to correctly position the cap on the pump diaphragm. They usually act independently of the rotary position of the cap relative to the pump diaphragm. For an orientation with regard to a rotary position, other elements may also be provided, for example a suction connector, however these have no influence on the tightness of the connection between cap and pump diaphragm.

A further object of the invention is to create a breast pump with which it is ensured that the breast pump enables an automatic pressure relief in the event of an overpressure.

This object is achieved by a breast pump having the features of claim 15.

The breast pump according to the invention for expressing human breast milk has a motor-driven flexible pump diaphragm and a rigid cap that can be put thereover, whereby a pump chamber for generating a negative pressure is formed between pump diaphragm and cap. The cap can be connected or is connected via a suction line to a breast shield unit. The negative pressure generated in the pump chamber can be transferred into the breast shield unit. By being rested indirectly or directly on the pump diaphragm the cap is airtightly connected thereto in order to form the pump chamber. A venting valve is provided in the cap and connects the pump chamber to an outside.

This type of venting is advantageous since the valve does not have to be arranged in the pump diaphragm. The pump diaphragm can thus move and deform better. The suction curves can be created more easily and in an optimized manner.

This venting valve can be used with the cap described in this text or also with another cap. By way of example, it can be used with a cap that rests tightly and/or fixedly on the pump diaphragm only with use of a protective diaphragm or another part arranged between cap and pump diaphragm, thereby forming the pump chamber and thereby being connected to the housing of the pump without any additional fastening points. In particular the venting valve can be used with a known cap of the Symphony pump in that the cap is supplemented accordingly by the valve. With this cap as well, no additional fastening means are needed. Especially, the cap does not have to be fixed to the housing of the pump with fixing means such as screws or retaining hooks. The cap is only connected with the pump diaphragm.

Further embodiments are specified in the dependent claims.

BRIEF DESCRIPTION OF THE DRAWINGS

Preferred embodiments of the invention are described hereinafter on the basis of drawings, which serve merely for explanation and are not to be interpreted as limiting. In the drawings.

Like parts are provided with like reference signs.

DESCRIPTION OF PREFERRED EMBODIMENTS

Figure 1:
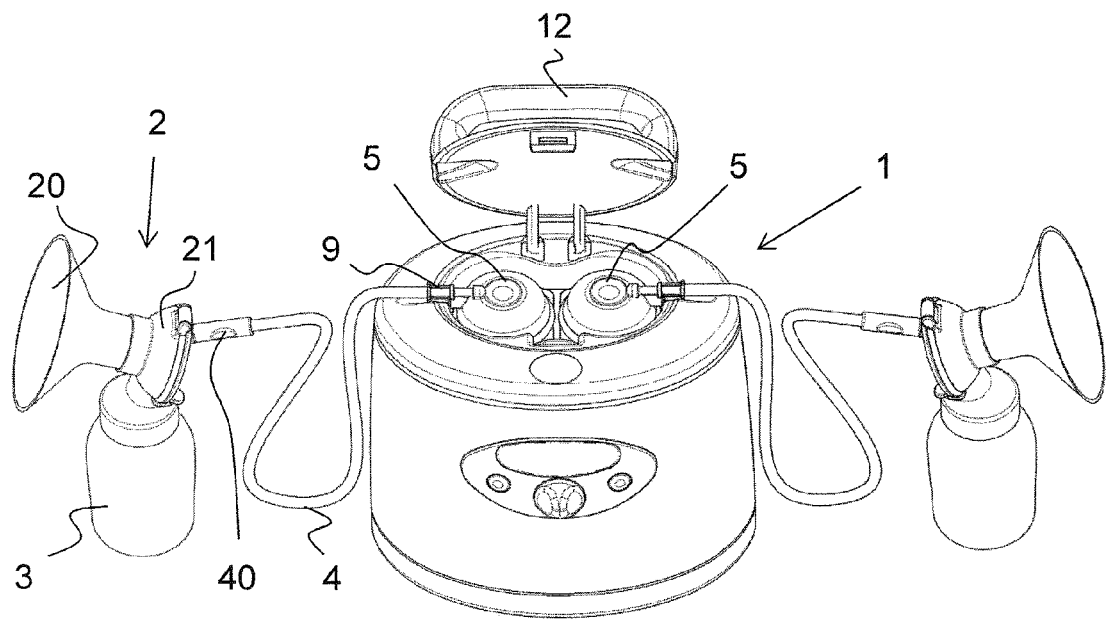
FIG. 1 shows a perspective illustration of a breast pump according to the invention with two caps according to the invention.

A breast pump unit having a breast pump 1 according to the invention is illustrated in FIG. 1. The breast pump 1 has a housing 10, which on the upper side thereof has an indentation 11. Two flexible pump diaphragms 6 are arranged in this indentation 11 and are connected via a driveshaft 14 to a pump mechanism driven by means of an electric motor.

Each pump diaphragm 6 has a fixing plate 62 running around the periphery of said pump diaphragm and, on the underside thereof, latching hooks 64. The driveshaft 14 is likewise connected fixedly, but removably to the pump diaphragm 6, a corresponding fastening groove 66 being provided in the pump diaphragm for this purpose. The fastening groove 66 is preferably located in the upper middle region of the main body 60, such that the driveshaft 14 acts along the longitudinal centre axis of the pump diaphragm 6. By means of these connections, the pump diaphragm is held in a fixed manner in the housing 10 of the breast pump 1 and is usually not removed from the housing 10 by the user.

Figure 2:
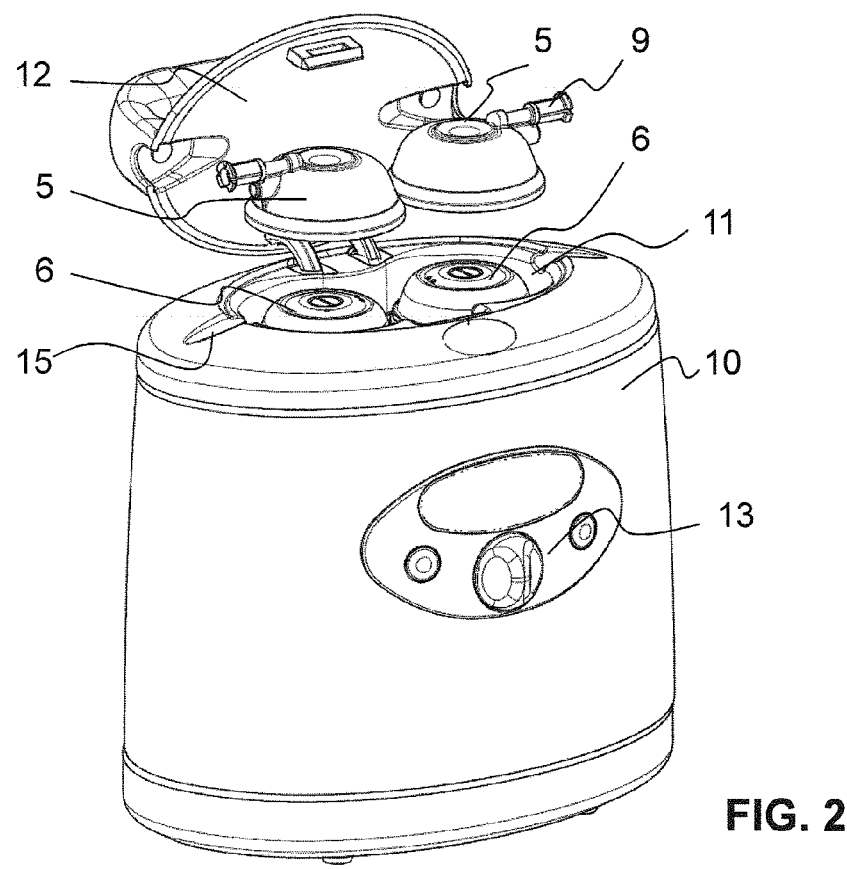
FIG. 2 shows the breast pump according to FIG. 1 with the two caps in the raised state.
Figure 3:
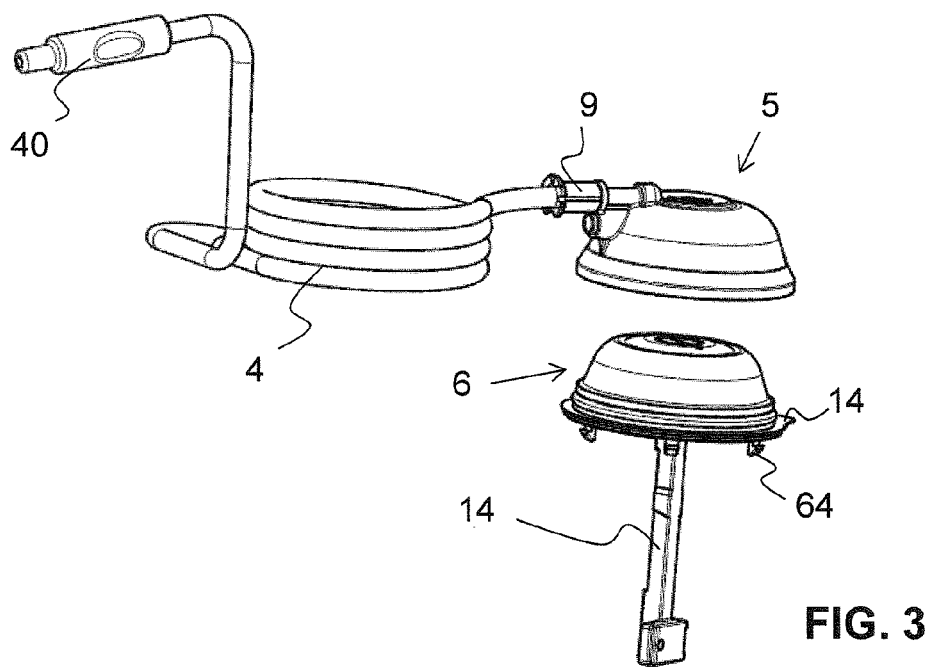
FIG. 3 shows a perspective illustration of the cap according to FIG. 1 with suction tube and a pump diaphragm with driveshaft.
Figure 6:
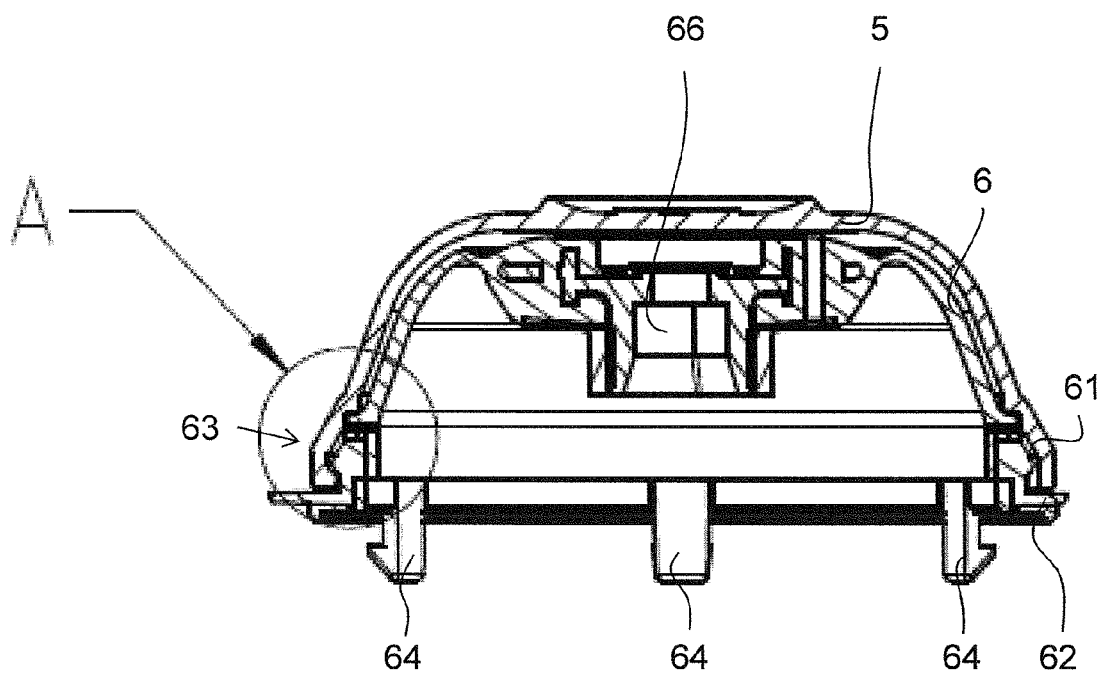
FIG. 6 shows a cross section through the cap and the pump diaphragm in the assembled state.

The pump mechanism is arranged in the housing 10. The other mentioned elements are illustrated in FIGS. 2, 3 and 6.

A cover 12 of the breast pump 1 closes the indentation 11 or makes it accessible from outside. A display and operating panel 13 arranged on an outer surface of the housing allows the user to activate the pump and to select the desired mode of operation thereof.

The breast pump also comprises at least one rigid cap 5. Here, two rigid caps 5 are provided. The caps 5 are preferably fabricated in one piece from plastic. Each cap 5 is put removably over one of the two pump diaphragms 6.

Each cap 5 is connected to a suction tube 4 either removably or fixedly and removably without destruction.

The suction tube 4 leads to a breast shield unit 2, and preferably can be plugged into this breast shield unit by means of a breast-shield-side coupling part 40.

The breast shield unit 2 has a connector 21 for connection to the suction tube 4 and a breast shield 20 for collecting the breast to be pumped. The breast shield 20 is either connected in one piece to the connector 21 or is held therein removably. The connector 21 also has a milk connection point for connection to a milk collection container, here a milk bottle 3.

The connection between vacuum or suction tube 4 and cap 5 is established via a cap-side coupling part 9. This coupling part 9 and/or the suction tube 4 may lie in a groove 15 of the housing 10 so that the cover 12 can be closed when the cap 5 is inserted. However, the apparatus also functions when the cover 12 is open. The caps 5 are not connected to the cover 12, but are separate parts, independent of the cover 12 and of the housing 10.

Figures 4, 5:
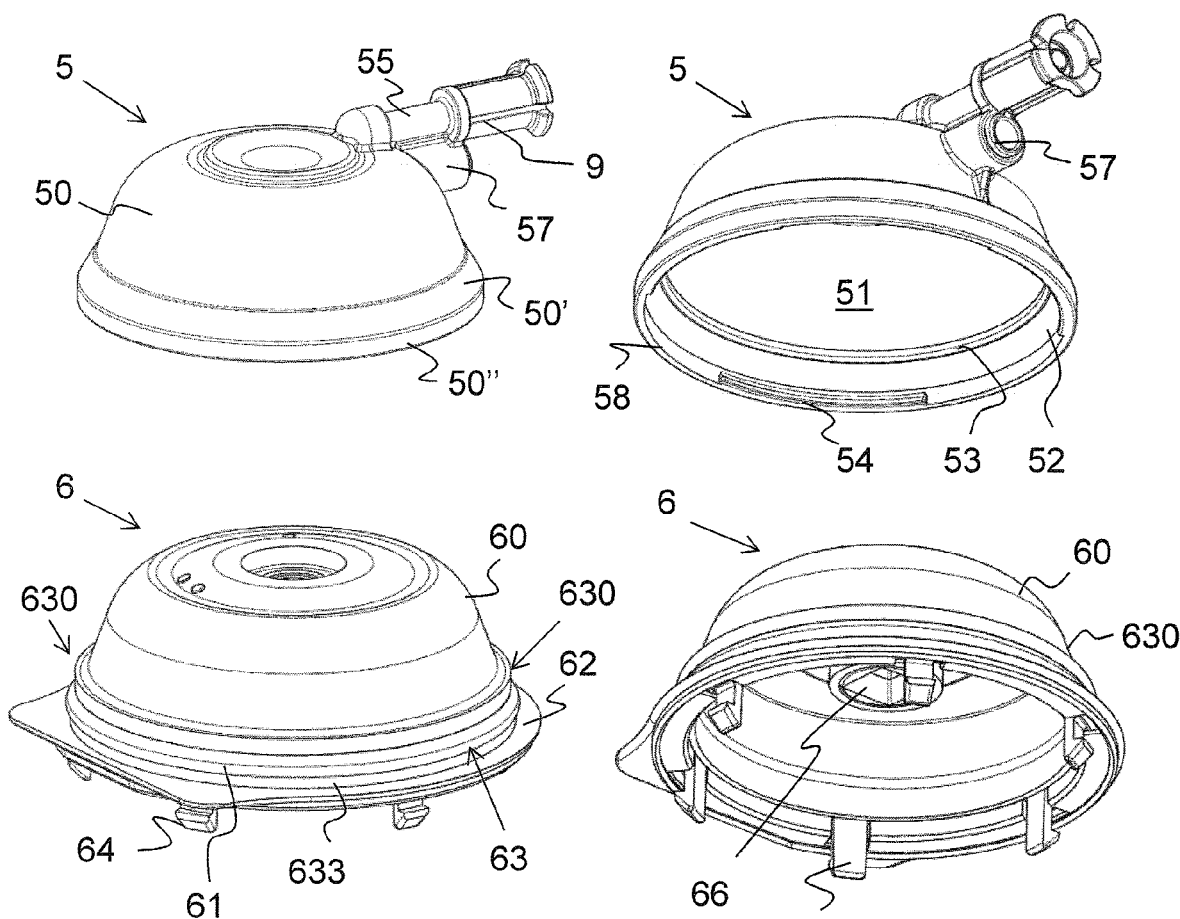
FIG. 4 shows an exploded illustration of the cap according to the invention and of the pump diaphragm in a view from above.
FIG. 5 shows an exploded illustration of the cap according to the invention and of the pump diaphragm in a view from below.

In FIGS. 4 and 5 the cap 5 and pump diaphragm 6 are illustrated individually. The cap 5 has a dome-shaped main body 50 with round cross section. The main body 50 transitions at the lower open end thereof into a chamfered region 50' widening outwardly. This chamfered region 50' ends in a circular-cylindrical region 50", which forms the lower end of the cap 5 and thus ends in an outermost edge.

A tube mount 55 is arranged on the cap 5 and is designed here simultaneously as a grip so that the cap 5 can be easily inserted into the indentation of the housing 1 and thus fitted onto the pump diaphragm 6 and also can be easily removed therefrom again. The tube mount 55 is connected to the cap-side coupling part 9.

A valve mount 57 is provided on the lower side of the tube mount 55. However, this can also be arranged in another region of the cap 5.

The cap 5 is internally hollow. The cavity is designated in FIG. 5 by reference numeral 51. The cap 5 and therefore the cavity 51 are open downwardly, wherein the access opening to the cavity 51 corresponds to the inner diameter of the outermost edge.

A closed bearing region 53, formed here by an inner bead as a shoulder, runs around an inner surface of the cap 5. This shoulder 53 is located preferably in the region of the transition from the main body 50 to the chamfered region 50' and is directed into the cavity 51. As can be seen clearly in FIG. 7 the shoulder 53 has, on the underside thereof, an approximately horizontally extending, circumferential face. This serves as a stop when it rests on a step 630, more specifically on a horizontal step face 631 or ledge of the pump diaphragm 6. The user thus notices that the cap 5 is fitted correctly on the pump diaphragm 6.

At least one form-fit element 54 is provided on the inner side of the circular hollow-cylindrical region 50". This form-fit element is formed as a snap-fit element 54. It preferably has the form of an inwardly directed bead, which is arranged close to or bordering on the outermost edge, i.e. the downwardly directed end face of the cap 5. If a number of snap-fit elements 54 are provided, they preferably extend at the same and/or uniform distance from the outermost edge.

Figure 9:
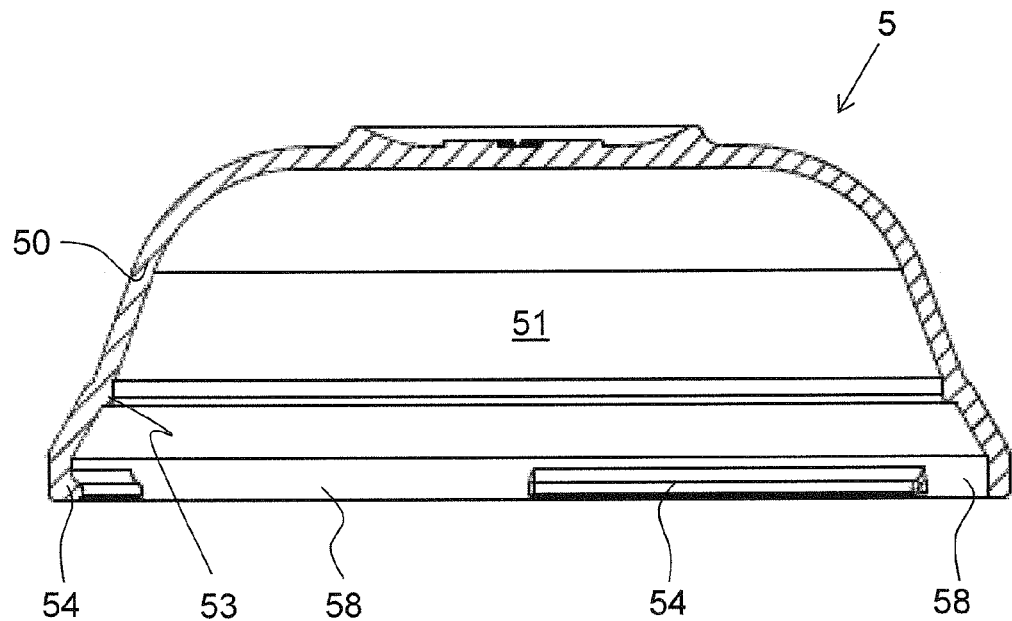
FIG. 9 shows another cross section through the cap according to FIG. 1.
Figure 10:
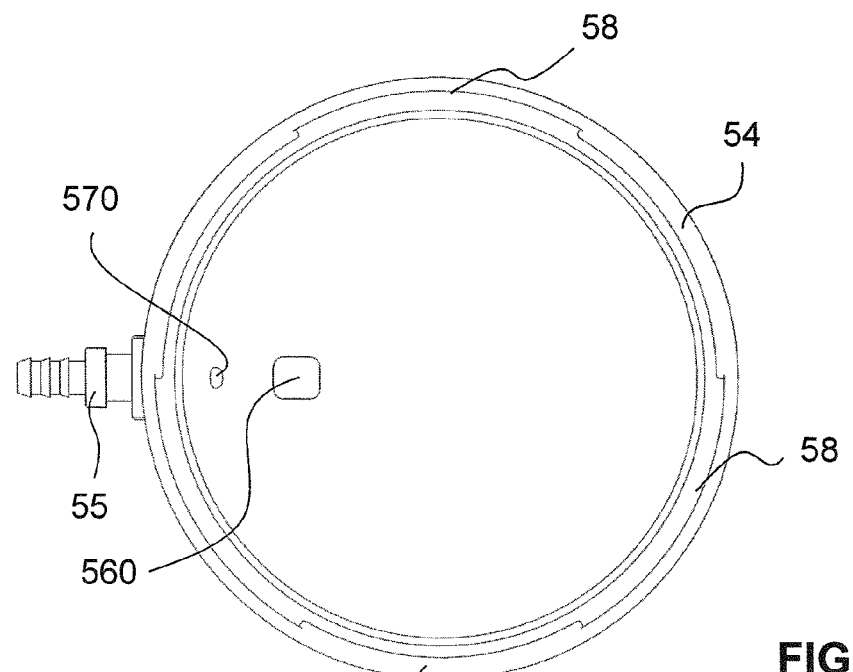
FIG. 10 shows a view of the cap according to FIG. 1 from below.

The at least one snap-fit element 54 runs around the inner surface of the cap 5. A number of snap-fit elements 54 are preferably provided and are separated from one another by interruptions 58. This can be clearly seen in FIGS. 9 and 10.

Figure 7:
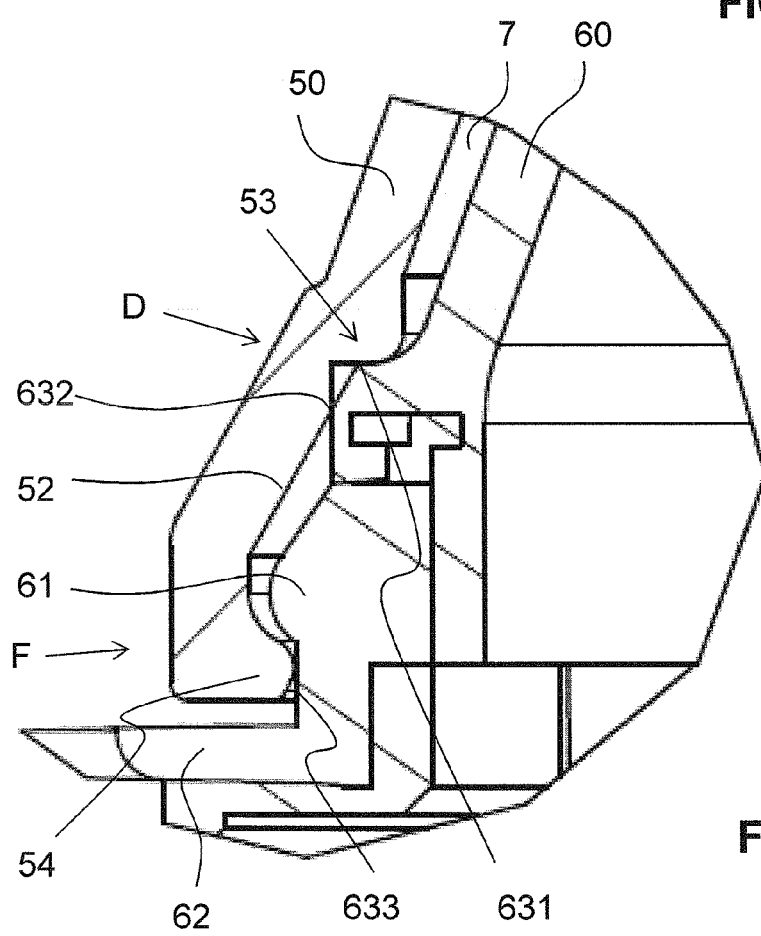
FIG. 7 shows an enlarged detail according to FIG. 6.

A channel 52 is formed between the shoulder 53 and the snap-fit elements 54, as can be clearly seen in FIGS. 5 and 7.

Figure 8:
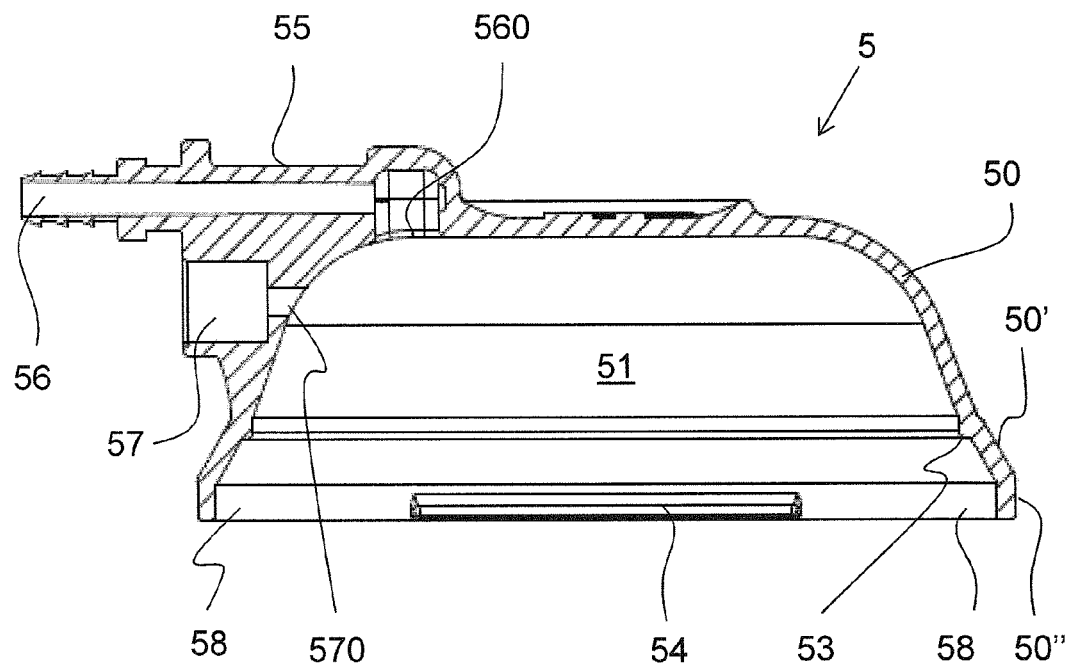
FIG. 8 shows a cross section through the cap according to FIG. 1.

In FIG. 8 the valve mount 57 is illustrated. It is formed by an outwardly leading circular-cylindrical opening, which transitions into an air channel 570 of smaller diameter. The air channel 570 opens out into the cavity 51 of the cap 5. The tube mount 55 is molded integrally on the cap 5 above the valve mount 57. The tube mount has a connection piece 56 for connection to the cap-side coupling part 9. The connection piece 56 has a channel, which leads outwardly via one end and transitions via another end into a suction opening 560 opening out into the cavity 51 of the cap 5.

Figure 11:
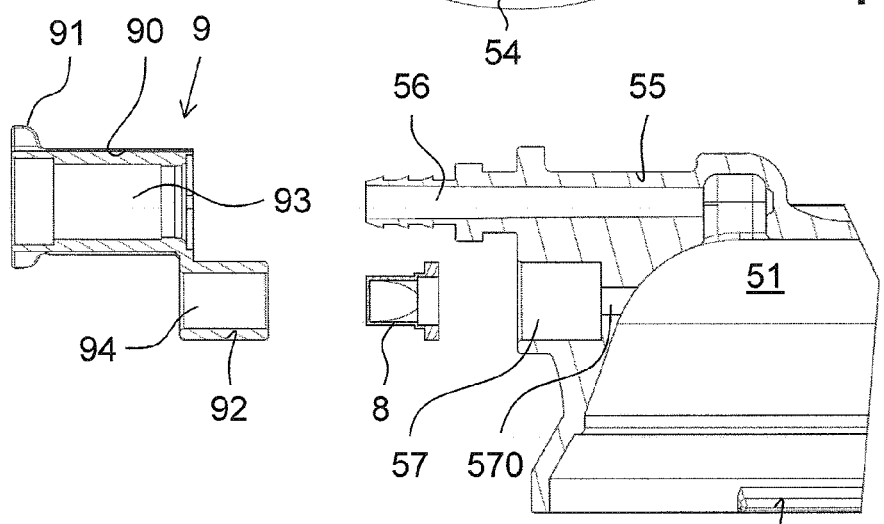
FIG. 11 shows an enlarged detail through the cap according to FIG. 1 and through a cap-side coupling part in an exploded illustration.
Figure 12:
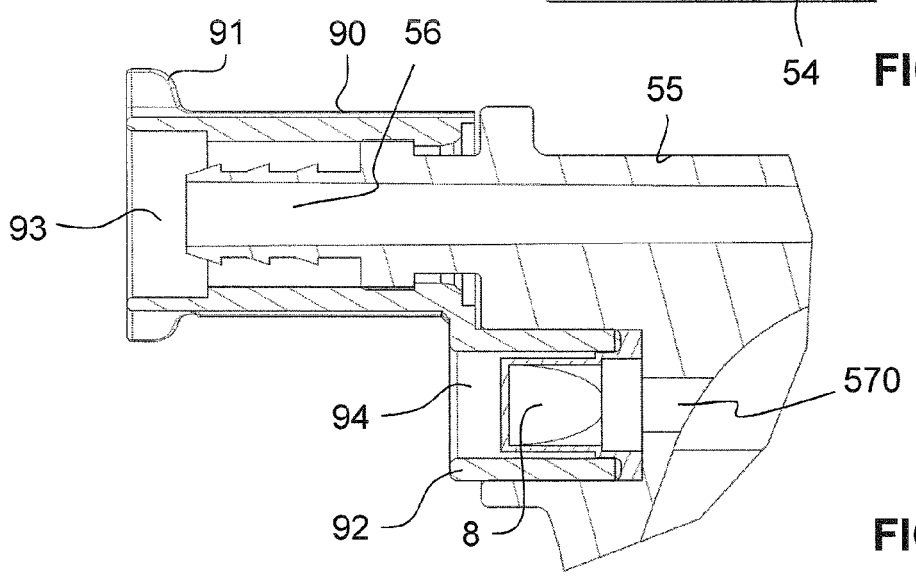
FIG. 12 shows the detail of the cap according to FIG. 11 with the coupling part in the assembled state.

The cap-side coupling part 9 can be clearly seen in FIGS. 11 and 12. It has a suction connection piece 90 with a suction channel 93 for connection to the connection piece 56 and the suction opening 560 of the cap 5.

The suction connection piece 90 is preferably slid over the connection piece 56, steps and retaining structures of the tube mount 55 and of the coupling part 9 preferably preventing the coupling part 9 from being able to be removed again without being destroyed. A slipover protection means 91, here in the form of a circular structure with interruptions in the periphery thereof, prevents a suction tube of larger diameter from being slid over this coupling part.

A valve connection piece 92 with an air channel 94 is preferably molded integrally in one piece on the cap-side coupling part 9. It is located preferably below the suction connection piece 90, wherein the air channel 94 extends parallel below the suction channel 93, but separately therefrom.

This valve connection piece 92 is used to accommodate a venting valve 8, here a check valve, preferably a duckbill valve. The valve connection piece 92 can be slid with the check valve 8 into the valve mount 57 when the cap-side coupling part 9 is fastened on the tube mount 55. The check valve 8 is held in a fixed manner in the cap 5. It opens from the cavity 51 outwardly, i.e. in the event of overpressure in the cavity 51 with respect to the atmosphere outside the cap 5. The cap 5 is otherwise preferably formed in one piece.

FIGS. 4 and 5 also clearly show the pump diaphragm 6. It has a dome-shaped main body 60, which preferably forms the counterpiece to the dome-shaped cavity 51 of the cap 5 and thus bears against the inner wall of the cap 5. The main body 60 transitions in the lower region thereof in a step into the circumferential and closed collar 63. The collar 63 has the step 630 and therefore the preferably horizontally running, upwardly directed step face 631 or the ledge. The collar 63 is preferably cylindrical in the upper region thereof and is present in the form of a vertically extending step face 632. It then has an outer bead 61, which protrudes outwardly and circumferentially and is also closed. The collar 63 preferably has a lower collar region 633 adjacent to the fixing plate 62, which collar region lies below the bead 61 and has a greater outer diameter than the region of the vertical step face 632.

In FIGS. 6 and 7 the cap 5 and the pump diaphragm 6 are illustrated in the assembled state. The cap 5 is put over the pump diaphragm 6, the snap-fit elements 54 protruding below the outer bead 61 and thus engaging therewith from behind. The cap 5 is thus snapped into place on the pump diaphragm 6 in a form-fitting manner. The form-fitting fixing region is characterized in FIG. 7 with the reference sign F.

If the cap 5 is installed and the snap-fit elements 54 are engaged with the outer bead 61, the shoulder 53 thus lies on the upper step face 631 of the collar 63. As can be seen in FIG. 7, this region together with the adjacent region of the channel 52 forms a frictional connection and thus the seal region D.

The cap 5 is thus held in a sealing manner directly on the pump diaphragm 6 without additional parts. A pump chamber 7 is formed in the cavity 51 of the cap 5 between the pump diaphragm 6 and cap 5. The volume of the pump chamber 7 is minimal or zero when the pump diaphragm 6 is in the dome-shaped basic form thereof.

This basic form is changed by the pump mechanism in that the driveshaft 14 draws the middle region of the main body 60 of the pump diaphragm 6 downwards. The main body 60 is thus deformed. If the driveshaft 14 pushes the main body 60 upwardly again, it reassumes its original form. The collar 63 is preferably not deformed, but is rigid. Due to the change in shape of the main body 60, the volume of the pump chamber 7 changes, a negative pressure is generated cyclically, and the pressure change is transferred into the breast shield unit 2 and to the breast shield 20.

If, during the first stroke, the pump diaphragm 6 is not yet in its basic form, but the air in the pump chamber 7 is first compressed, the venting valve 8 is used. The air can escape from the valve 8 and the pump is then immediately ready for use without the user having noticed anything. If, during the first stroke, the pressure in the pressure chamber 7 is too high, the air additionally escapes through the interruptions between the snap-fit elements 54.

Figure 13:
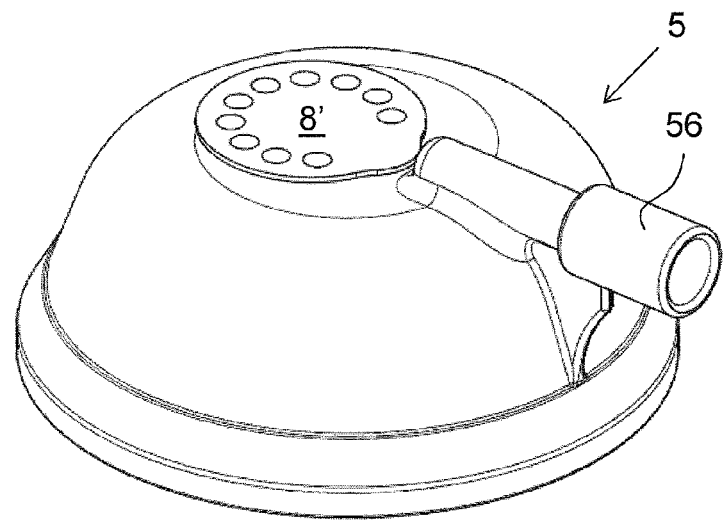
FIG. 13 shows a perspective illustration of a cap according to the invention in a second embodiment.
Figure 14:
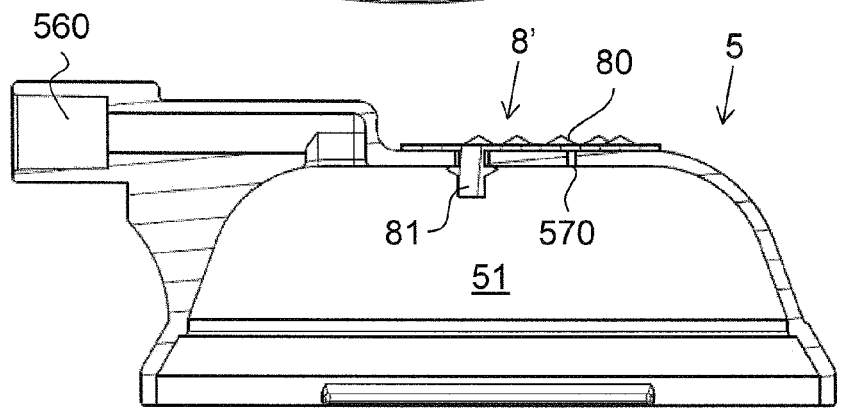
FIG. 14 shows a cross section through the cap according to FIG. 13.

In FIGS. 13 and 14 a cap 5 with an alternative venting valve 8' is illustrated. It is a diaphragm flap 80 with a fastening stub 81, which is held in a recess in the upper wall of the cap 5. The diaphragm flap 80 here covers the air channel 570 of the cap 5, which penetrates the upper wall of the cap 5 and leads outwardly from the cavity 51.

Figure 15:
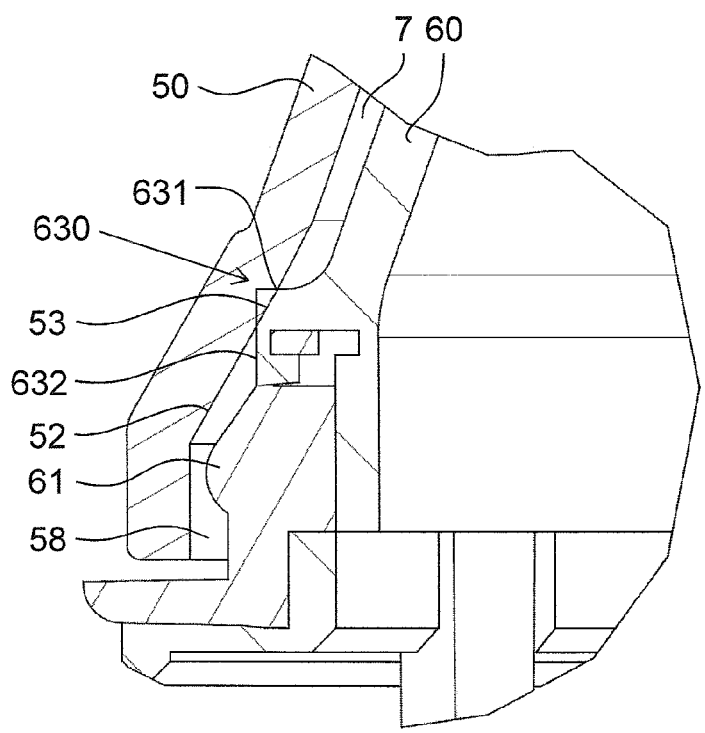
FIG. 15 shows an enlarged detail of a cross section through a cap according to the invention in a third embodiment.

In FIG. 15 a further embodiment is illustrated, which is formed without venting valve or which can be provided with one of the valves 8, 8' according to the above-described embodiment. In this embodiment the cap 5 on the inner side thereof does not have a shoulder, but a bearing face extending at a continuous incline in cross section, which bearing face forms the bearing region 53. This circumferential bearing face 53 forms a frictional connection with the edge of the step 630. The snap-fit elements 54 already described are again provided on the lower edge of the cap 5, wherein, in the illustration according to FIG. 15, the section through one of the interruptions 58 is illustrated.

The breast pump according to the invention and the rigid cap according to the invention allow an airtight and easily producible connection between the cap and a flexible pump diaphragm in order to form a pump chamber.

The invention claimed is:

1. A breast pump for expressing human breast milk having a motor-driven flexible pump diaphragm and a rigid cap that is configured to be put over the flexible pump diaphragm, whereby a pump chamber for generating a negative pressure is formed between the pump diaphragm and the cap, the cap being connectable or connected via a suction line to a breast shield unit, and the negative pressure generated in the pump chamber being transferrable into the breast shield unit, the pump diaphragm having a circumferential collar with a step and having a laterally projecting protrusion, and the cap having, on the inner side thereof, a circumferential bearing region, the cap has, on the inner side thereof, at least one form-fit element, which is arranged at a distance from the circumferential bearing region and which together with the protrusion of the pump diaphragm forms a form fit, whereby the cap rests on the pump diaphragm in a manner snapped into place, and wherein the circumferential bearing region of the cap and the pump diaphragm in the region of the step are involved in a joint frictional connection and form a seal, such that the resting of the cap on the pump diaphragm in a manner snapped into place is sufficient to hold the cap in a sealing manner on the pump diaphragm, wherein the at least one form-fit element is a snap-fit element, which engages below the protrusion of the pump diaphragm.

2. The breast pump according to claim 1, a circumferential channel being formed between the circumferential bearing region and the at least one form-fit element and surrounding the collar of the pump diaphragm and receiving the protrusion.

3. The breast pump according to claim 1, no additional parts being arranged between the cap and the pump diaphragm.

4. The breast pump according to claim 1, a venting valve being provided, which connects the pump chamber to an outside.

5. The breast pump according to claim 4, the venting valve being arranged in the cap.

6. The breast pump according to claim 1, a venting valve being provided, which is arranged in a plug connecting the suction line to the cap or in the breast shield unit or in the suction line.

7. A cap for use in a breast pump for expressing human breast milk, the breastpump having a motor-driven flexible pump diaphragm, wherein the cap is rigid and is configured to be put over the flexible pump diaphragm, whereby a pump chamber for generating a negative pressure is formed between the pump diaphragm and the cap, the cap being connectable or connected via a suction line to a breast shield unit, and the negative pressure generated in the pump chamber being transferrable into the breast shield unit, the pump diaphragm having a circumferential collar with a step and having a laterally projecting protrusion, and the cap having, on the inner side thereof, a circumferential bearing region, wherein the cap has, on the inner side thereof, at least one form-fit element, which is arranged at a distance from the circumferential bearing region and which together with the protrusion of the pump diaphragm forms a form fit, whereby the cap rests on the pump diaphragm in a manner snapped into place, and wherein the circumferential bearing region of the cap and the pump diaphragm in the region of the step are involved in a joint frictional connection and form a seal, such that the resting of the cap on the pump diaphragm in a manner snapped into place is sufficient to hold the cap in a sealing manner on the pump diaphragm, the at least one form-fit element being designed as a snap-fit element and the at least one form-fit element being formed by an inwardly directed bead.

8. The cap according to claim 7, wherein the cap has a dome-like main body and a circumferential outermost edge, the at least one form-fit element being arranged on the inner side of the outermost edge of the cap.

9. The cap according to claim 8, the dome-like main body transitioning into an edge region that is chamfered in a manner widening outwardly and which transitions into a cylindrical edge region, the cylindrical edge region ending in the outermost edge.

10. The cap according to claim 9, the circumferential bearing region being formed in a transition region from the main body into the chamfered edge region.

11. The cap according to claim 8, the outermost edge being circular.

12. The cap according to claim 8, the at least one form-fit element being formed in a manner running around a periphery of the inner side of the cap.

13. The cap according to claim 7, the at least one form-fit element is a plurality of form-fit elements, the plurality of form-fit elements running around a periphery of the inner side of the cap and being separated from one another in the periphery of the inner side by interruptions.

14. The cap according to claim 13 wherein the plurality of form-fit elements are separated from one another in the periphery of the inner side by exactly three interruptions.

15. A breast pump for expressing human breast milk having a motor-driven flexible pump diaphragm and a rigid cap that is configured to be put over the flexible pump diaphragm, whereby a pump chamber for generating a negative pressure is formed between the pump diaphragm and the cap, the cap being connectable or connected via a suction line to a breast shield unit, and the negative pressure generated in the pump chamber being transferrable into the breast shield unit, the pump diaphragm having a circumferential collar with a step and having a laterally projecting protrusion, and the cap having, on the inner side thereof, a circumferential bearing region,
wherein the cap has, on the inner side thereof, at least one form-fit element, which is arranged at a distance from the circumferential bearing region and which together with the protrusion of the pump diaphragm forms a form fit, whereby the cap rests on the pump diaphragm in a manner snapped into place, and wherein the circumferential bearing region of the cap and the pump diaphragm in the region of the step are involved in a joint frictional connection and form a seal, such that the resting of the cap on the pump diaphragm in a manner snapped into place is sufficient to hold the cap in a sealing manner on the pump diaphragm, wherein a circumferential channel is formed between the circumferential bearing region and the at least one form-fit element, surrounding the collar of the pump diaphragm and receiving the protrusion.

* * * * *